United States Patent [19]
Johnson

[11] Patent Number: 6,074,209
[45] Date of Patent: Jun. 13, 2000

[54] REDUCED TORQUE ENDODONTIC FILE

[75] Inventor: William B. Johnson, Tulsa, Okla.

[73] Assignee: Tulsa Dental Products Inc., Tulsa, Okla.

[21] Appl. No.: 09/166,881

[22] Filed: Oct. 6, 1998

[51] Int. Cl.$^7$ ................................................. A61C 5/02
[52] U.S. Cl. ............................................................ 433/102
[58] Field of Search ............................... 433/102, 81, 224

[56] References Cited

U.S. PATENT DOCUMENTS

| | | | |
|---|---|---|---|
| 1,022,838 | 4/1912 | Funk | 433/102 |
| 4,260,379 | 4/1981 | Groves et al. | 433/102 |
| 4,758,156 | 7/1988 | Johnson | 433/81 |
| 4,889,487 | 12/1989 | Louaas | 433/102 |
| 4,894,011 | 1/1990 | Johnson | 433/81 |
| 4,934,934 | 6/1990 | Arpaio, Jr. et al. | 433/102 |
| 5,035,617 | 7/1991 | McSpadden | 433/102 |
| 5,118,297 | 6/1992 | Johnson | 433/224 |
| 5,149,268 | 9/1992 | Johnson | 433/224 |
| 5,628,674 | 5/1997 | Heath et al. | 451/48 |
| 5,653,590 | 8/1997 | Heath et al. | 433/102 |
| 5,735,689 | 4/1998 | McSpadden | 433/102 |
| 5,735,690 | 4/1998 | Malentacca | 433/102 |

FOREIGN PATENT DOCUMENTS 520192  12/1992  European Pat. Off. ............... 433/102

*Primary Examiner*—Ralph A. Lewis
*Attorney, Agent, or Firm*—James B. Bieber

[57] ABSTRACT

An improved file for use in the endodontic preparation of a root canal, the file having a handle portion at one end and an active working portion tapering toward the distal end, the active portion having an external surface with at least one helical flute forming a helical scraping edge and, preferably, an axially adjacent land, the working portion having areas or zones of reduced surfaces that contact root canal surfaces during use. Preferably the zones are a plurality of axially spaced zones of reduced diameter so that the total length of file working portion in contact with canal wall surfaces during use is reduced. In manufacturing the improved file, a plurality of axially spaced zones of reduced diameter are formed on the working portion of a conventional file, including helical flutes and lands as desired, wherein the file of the invention includes an undulating external working portion profile.

17 Claims, 3 Drawing Sheets

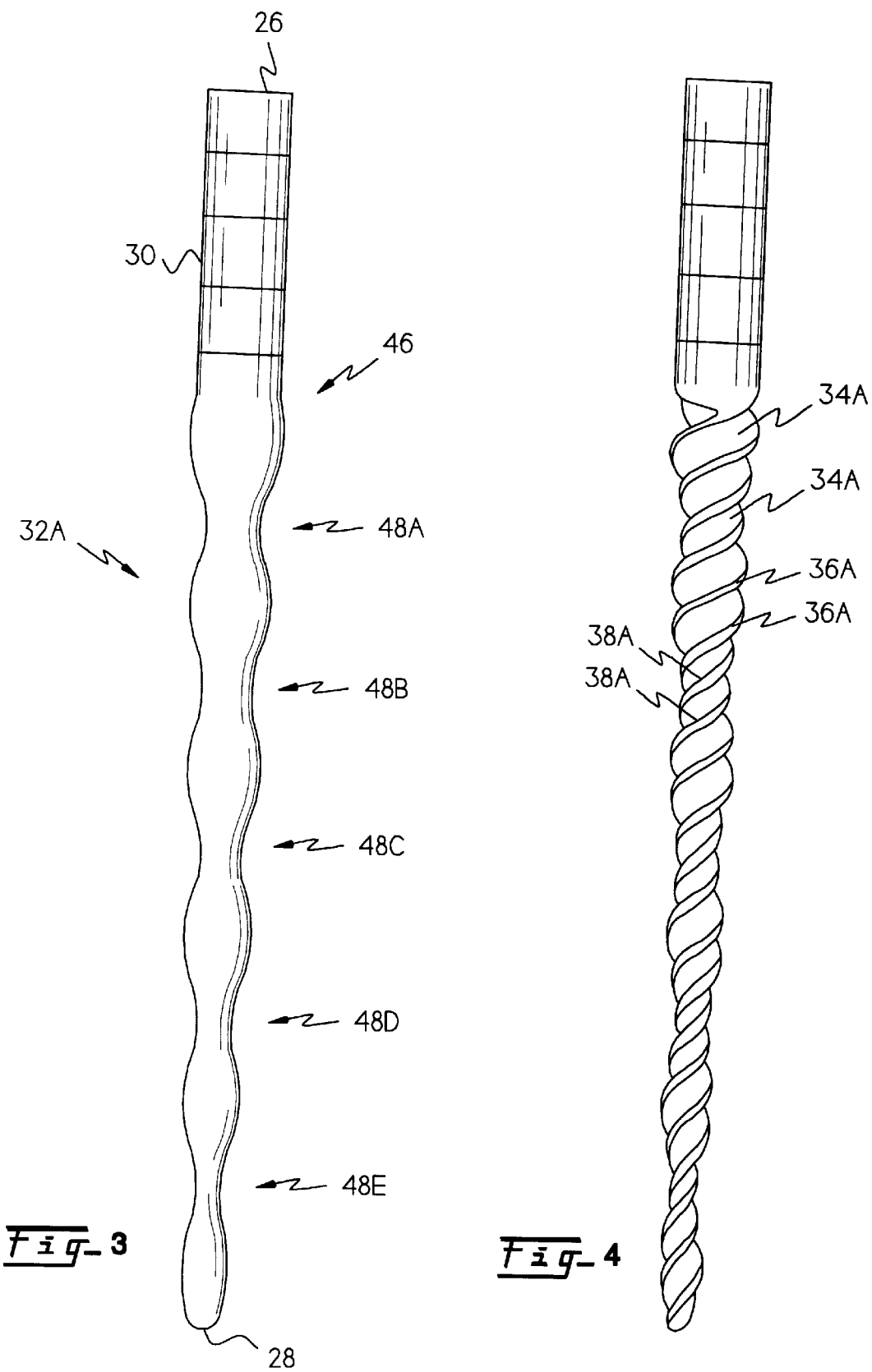

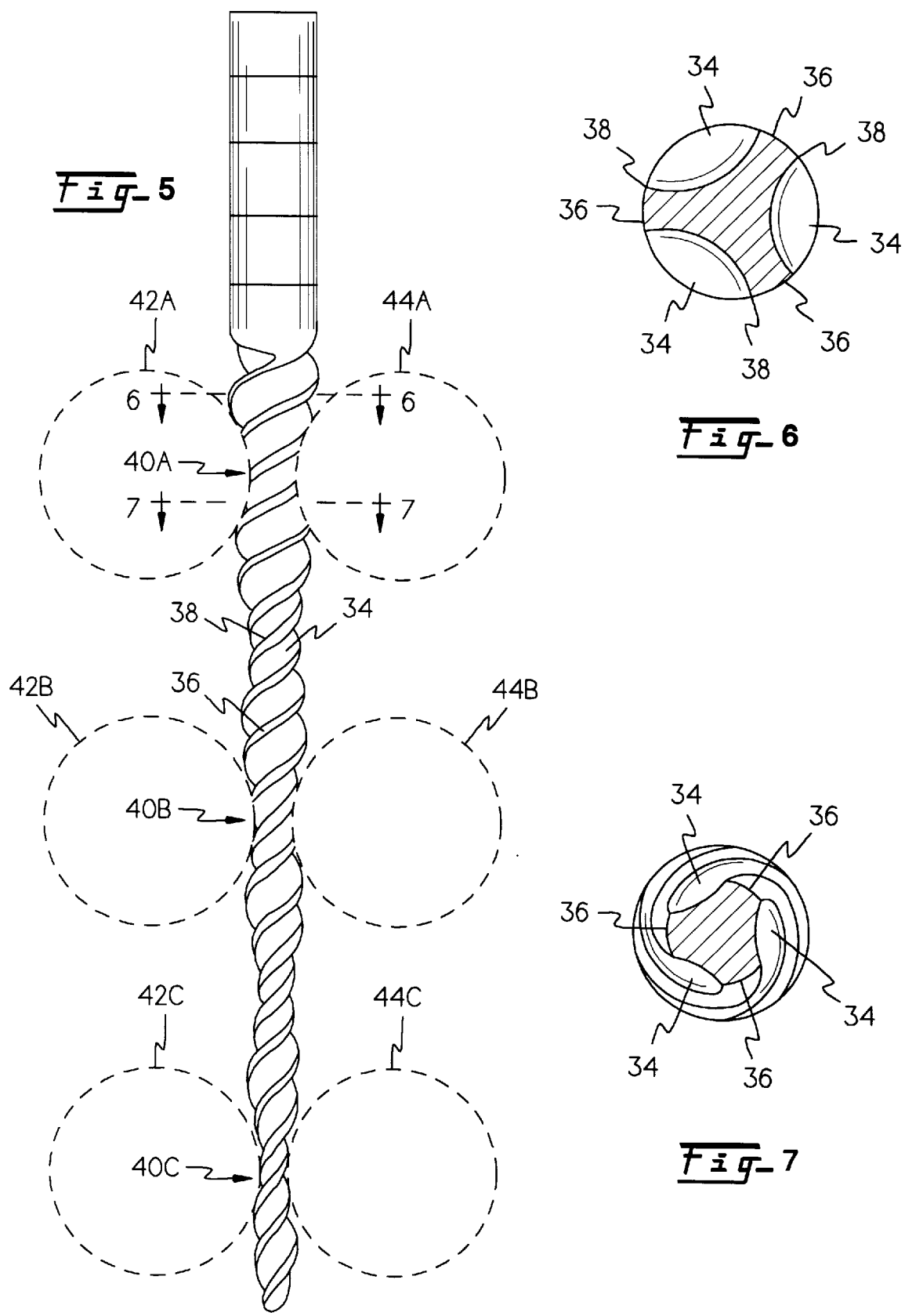

REDUCED TORQUE ENDODONTIC FILE

BACKGROUND OF THE INVENTION

This invention relates broadly to the field of endodontics and particularly to endodontic files for use in preparing root canals to receive obturating material.

When a root canal of a living tooth becomes infected or abscessed, discomfort and, in many cases, sever pain begins. In the early days of dentistry the only solution was to pull the tooth. However, in recent years the science of endodontics has developed wherein practitioners can successfully remove the pulp material forming the nerve of the tooth that has become infected and, after careful preparation of the canal that contained the nerve material, refill the canal with an inert obturating material, such as gutta percha, permitting a patient to retain the tooth. In order to achieve a successful root canal restoration, the dental practitioner must carefully and, as completely as possible, remove the pulpal material making up the nerve system of the tooth to thereby prevent continued or future infection of remaining tissues. Further, the removal process must typically include shaping of the root canal so that it can be more effectively and successfully refilled and sealed with an inert obturating material to eliminate the possibility of further infection occurring within the cleaned and shaped root canal.

Cleaning and shaping the root canal to receive obturating material is achieved by the use of metal files that include cutting or scrapping working surfaces for removing tissue in the root canal. The working surfaces are typically formed by helical or spiral flutes cut therein. Generally more than one flute is provided, often axially spaced to create a land therebetween to reduce aggressive cutting into the canal sidewalls.

Typical prior art files are described in U.S. Pat. No. 4,934,934, U.S. Pat. No. 5,628,674 and U.S. Pat. No. 5,653,590, which patents are herewith incorporated by reference.

Since root canals are seldom straight, often having bends and twists, the endo files must be flexible. Thus, materials of construction have evolved from stainless steel to nickel-titanium alloys that have enhanced flexibility yet are further characterized as being strong and not likely to fail in use. It is obviously essential to a successful root canal procedure to avoid file breakage during the cleaning process.

The files may be designed to be manually manipulated or to be "engine driven", that is, fitted to a handpiece that provides rotation of the file during its use. An endodontic file that is intended for hand use is typically provided with an enlarged diameter plastic handle attached to the file metal shaft, configured for easy manipulation between the thumb and forefinger of the practitioner. A file intended for use with a handpiece has a shaft portion or stem at the file proximal end configured to be removably received within a chuck of the handpiece, by which the file may then be rotated as desired by a practitioner.

It has recently become apparent that a root canal can be more successfully cleaned, shaped and filled if the completed canal tapers into a conical shape from the coronal area of the tooth towards the tooth apex, the canal cleaning and shaping procedure being advanced from the crown down to the apex. That is, it is easier to achieve complete cleaning and shaping and successful filling of a canal if the canal is tapered in a generally conical configuration rather than being of substantially no taper or approximating natural taper from the top to the apex. For this reason, a preferred endodontic file is tapered over its active or working portion, the tapering extending from its maximum diameter adjacent the proximal end to a minimum diameter at the file distal end. While conventional files were once limited to a standard taper of 0.02 mm/mm of working length of 16 mm, files are now often preferred to be of a greater taper, such as 0.04, 0.05, 0.06, which greatly aids in preparing the canal "crown-down" to achieve an optimal conical canal shape.

In current endodontic practice, a series of files of increasing diameters and/or tapers are used as the practitioner gradually cleans and shapes a root canal. The practitioner selects files with the goal of achieving the most optimal configuration of a prepared root canal, that is, a canal conically tapered from the tooth coronal area to a smallest diameter at the tooth apex.

In preparing the root canal, after opening and cleaning the crown and its adjacent pulp chamber, the practitioner often first selects a file having a greater taper than 0.02 mm/mm of length. In the engine driven procedure the file is rotated at low speed and advanced into the root canal opening. The file working surfaces cut, scrap or plane canal walls, first engaging only a limited portion of the canal walls. The scraping surfaces become more and more engaged as the file advances and the canal surfaces conform to the conical shape of the file. More and more torque must be applied to the file to overcome increasing frictional forces and to turn the file at desired speed as the file advances. Typically, the practitioner advances the file until the resulting frictional forces have substantially reduced the ease of further advancement. Further advancement raises the danger of stalling or locking-up the file. In such event, torque applied to the file may suddenly increase and the file could fail and break, leaving the practitioner with an extremely difficult extraction.

It would be an improvement in the art of endodontics to provide a file that has a reduced tendency to stall or lock-up when engaged in cleaning a root canal. Such a file would have a reduced torque input capability that limits torque that can be applied to the file such that the risk of a catastrophic failure is reduced or eliminated.

SUMMARY OF THE INVENTION

The present invention is a uniquely shaped endodontic file, permitting a practitioner to form crown-down, a conically shaped root canal, wherein sudden development of substantially increased rotating torque input to the file as it is advanced in the canal is substantially avoided. Thus, the present invention is an endodontic file having a reduced risk of stalling or locking-up developing during manipulation or rotation of the file in a root canal. More specifically, the file achieves reduced torque input by comprising along its working portion (i.e. its cutting or scrapping surfaces or edges) areas of reduced contact of the file scraping or cutting edges with the root canal wall surfaces, preferably achieved by zones of reduced diameter. The areas or zones of reduced surface contact substantially reduce the likelihood of inputting excessive torque to the file, since the possibility of frictional forces causing the file to tend to stall or lock-up are greatly reduced.

A file of the invention is formed of an elongated metal shank having a proximal end that is adapted either for manual or handpiece manipulation or rotation and an active working portion extending in a desired taper to a reduced diameter distal end. The file working portion or surfaces includes at least one spiral flute forming cutting or scraping edges and preferably axially adjacent spiral lands. The external surfaces of the file active working portion of the file of this invention further include at least one, and preferably a plurality of, axially spaced zones of reduced diameter. Alternatively, portions of the working surfaces may be removed randomly or in patterns, whereby working surfaces are removed sufficiently to reduce frictional contact with canal walls, while cutting efficiency is adequately maintained.

The dimensions of the areas or zones of reduced diameter are characterized by axial length, depth and profile such that frictional forces acting on the file at full engagement with root canal surface are significantly reduced. Preferably, the file of the invention including a plurality of such zones, comprises a file working portion having an undulating profile.

A method of manufacturing the reduced torque endodontic file of this invention includes providing an elongated tapered shank having a working portion on which is formed at least one helical spiral flute having active scraping edges and axially adjacent lands, followed by forming a series of axially spaced reduced diameter circumferential zones of desired depth, axial length and profile onto the file active surface.

An alternative method of manufacturing an improved endodontic file of this invention includes providing an elongated metal shank having a handle or a chuck receiving portion at the proximal end and having an active working portion that tapers from adjacent the proximate portion to a reduced diameter distal end. The working portion of the file is further machined or cold rolled or otherwise treated to form the desired axially spaced circumferential grooves or undulating profile in the file working portion. Thereafter, at least one spiral flute and land is formed in the working portion of the file, the spiral flute resulting in the formation of at least one active scraping or cutting edge thereon.

A better understanding of the invention will be obtained from the following description of the preferred embodiments and the claims, taken in conjunction with the attached drawings.

BRIEF DESCRIPTION OF THE DRAWINGS

FIG. 3 shows a partially prepared blank of an embodiment of the invention having an undulating working surface profile, before flutes are formed therein.

FIG. 4 shows the finished file of FIG. 3, after helical flutes have been formed on the file external working surface, completing the embodiment of the invention.

FIG. 5 shows, diagrammatically, modification of an endodontic file to provide zones of reduced external diameter, providing an embodiment of the invention.

FIG. 6 is a transverse cross-sectional schematic view, taken along the line 6—6 of FIG. 5.

FIG. 7 is a transverse cross-sectional schematic view taken along the line 7—7 of FIG. 5, showing a circumferential zone wherein the external diameter has been reduced.

DETAILED DESCRIPTION OF THE DRAWINGS

Figures 1, 2:
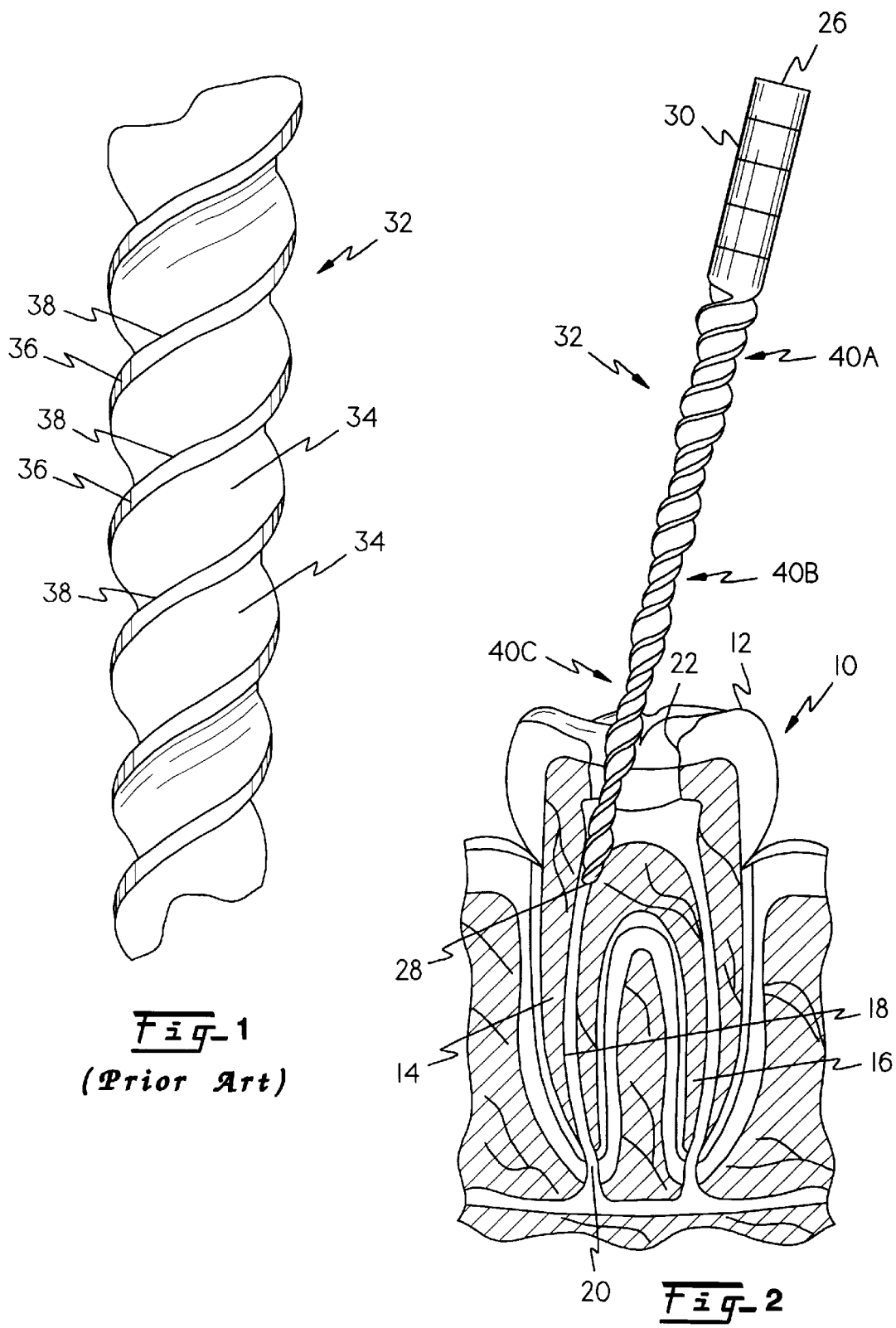
FIG. 1 is a fragmentary elevational view of a typical prior art file of the type used for the endodontic preparation of a tooth.
FIG. 2 is an elevational view of a tooth, such as a molar, having a plurality of root canals and showing an improved endodontic file of this invention as it is poised for use to shape the root canal, the file illustrated being greatly enlarged relative to the size of the illustrated tooth.

Referring to the drawings, FIG. 1 shows an elevational view of a portion of a endodontic dental file of a prior art type that is commonly in current use. The file includes a plurality of axially adjacent helical or spiral flutes 34 formed in the working portion 32 external surfaces of the file. The flutes may be axially spaced such that spiral radial lands 36 are formed between the flutes. Each of the spiral flutes provides an active cutting or scraping or planing edge 38 that, upon rotation and advancement of the file in the root canal, scrapes pulpal and other material from root canal surfaces. Further, the file active surfaces shape and enlarge the root canal by scraping or cutting away portions of the root canal walls.

Referring to FIG. 2, a cross-section of a representative tooth 10 is shown having a crown or conical area 12, a first root portion 14 and a second root portion 16. The first root portion 14 has a root canal 18 that begins in the coronal area and ends at the root apex 20. In the endodontic treatment of a tooth having more than one root canal, it is normally necessary that all of the root canals of the tooth be treated. However, for illustrative purposes herein only the root canal of the first root portion 14 will be discussed.

To treat a tooth wherein a root canal has become infected or abscessed, an endodontist or dental practitioner, first forms an opening 22 in the crown area to provide access to the root canal. Pulpal material must then be removed and the root canal thoroughly cleaned. Further, the root canal 18 needs to be shaped to receive obturating material, such as gutta percha, after which the opening 22 in the crown area of the tooth is filled.

To remove pulpal material from the root canal 18 and to shape it to facilitate sealing with obturating material, endodontic files of the type generally discussed above and in the above cited patents, are used. A file of this invention is shown in FIG. 2, said file having a proximal end 26 and a distal end 28. Adjacent the proximal end 26 is a handle or chuck that is designed and manufactured to be manipulated manually or rotated in a dental handpiece. The file is configured with a chuck stem 30 for placement in the chuck of a dental handpiece by which the file can be manipulated and rotated at a desired speed. Below the chuck stem portion 30 and extending to distal end 28 are the file active surfaces or working portions 32 that function to clean and shape the root canal 18.

FIGS. 3 and 4 show details of a preferred embodiment of the invention. FIG. 3 shows an elongated metal shank file blank 46 for use in making a finished file of the invention shown in FIG. 4. The blank 46 has a chuck stem 30, proximal end 26, distal end 28 and has a tapered active working portion 32A. The active portion of the file blank 46 is tapered as desired, such as 0.04 mm/mm of length. However, the tapered surface has been provided with a plurality of zones 48A–48E of reduced diameter (40A–C, in FIG. 2), a key element of this preferred embodiment of the invention. The reduced diameter zones are all formed circumferentially about the blank 46 and are individually arcuate in profile, in sum imparting an undulating profile to the blank. The blank may be prepared by machining, cold rolling or by any other suitable metal working processes, which are well known in the metal working arts.

After the blank 46 has been prepared with the tapered active or working portion having axially spaced circumferential zones of reduced diameter as, shown in FIG. 3, flutes 34A, lands 36A and active scraping edges 38A are then formed on the undulating tapered exterior surface of the file active portion 32A to form the finished endodontic file of FIG. 4. That is, the formed or machined blank 46 of FIG. 3 is subjected to manufacturing steps wherein at least one flute 34A, but preferably a plurality of flutes, is formed in the undulating exterior surface. The flutes may be axially spaced serving to provide lands 36A and leading edges 38A so that the finished file has a tapered working portion of flutes, lands and active edges that decrease in external diameter in the direction towards distal end 28, but wherein the decrease in diameter is made variable by the zones of reduced external diameter.

In operation, the file of the invention is utilized in a manner identical to the use of any endodontic file of greater than 0.02 taper. The file is rotated at a desired low speed and advanced into contact with root canal wall surfaces. When the file cannot be easily advanced further; that is, significantly resists further advancement because its working surfaces are substantially full engaged, the file is then withdrawn and another selected. The file of the invention may be more confidently used at full advancement due to the zones of reduced diameter since by their lack of contact with canal wall surfaces frictional forces exerted on the rotating file working surfaces are reduced. The danger of the frictional forces suddenly stalling or locking-up the file are greatly reduced or eliminated. The result is that it is less likely that a sudden increase in torque will be inputted to the file which could cause the file to break.

It is noted that varying certain characteristics of the reduced diameter zones such as their periodicity and axial distribution on the file working surfaces may enhance file performance. Such variation may add to the likelihood of the file avoiding excess torque input through lock-up.

Referring now to FIG. 5, one example of a method of manufacturing a file that meets the requirement of this invention is illustrated. FIG. 5 shows a file substantially identical to that of FIG. 4 wherein the formation of circumferential zones 40A–C of decreased external diameter is achieved by rotating grinding wheels 42A–C and 44A–C. The result is that, at the zones 40A–C of the file, the external diameter of the file is decreased as compared with the file working portions above and below the wheels.

Preferably, the file is rotated axially as the zones are formed such that the zones extend completely about the circumference of the file. As illustrated in FIG. 6, the flutes 34, lands 36 and active scraping edges 38 remain at the full diameter of the file at the point where the cross-section 6—6 is taken. In contrast, the cross-sectional view of FIG. 7 shows that portions cut away by the grinding wheels 42 and 44 provide a configuration wherein the lands 36 have been reduced in height, reducing the depth of flutes 34. The principals of this invention apply to a file irrespective of the specific geometrical design of flutes 34, lands 36 and active edges 38. "Scraping edge" as used hereinafter also includes any cutting or planing edges.

Any process of manufacturing which results in a change in the external circumferential profile of the file that reduces the area of contact of the file active edges or lands as the file is rotated or longitudinally manipulated within a root canal is within the purview of this disclosure.

An alternative embodiment (not shown in the drawings) of the invention, for example, comprises a file in which "pot holes" have been drilled or formed into the file working surfaces to reduce surface area that contacts canal walls. Such pot holes are placed in random or selected patterns whereby contact surfaces are reduced, but sufficient cutting efficiency is maintained. These working surfaces are, for example, prepared by drilling small diameter blind holes into the working surfaces, before or after tapering or a flute is formed.

The endodontic file of the invention, as illustrated above is advantageous in that the possibility of the development of excessive torque in the file is minimized since contact of the file active scraping edges and lands with the root canal wall is reduced. The reduction is particularly important as the root canal is cleaned and shaped such that the canal walls approach a tapered configuration that approaches that of the taper of the file itself It can be seen that when a file as described herein is used in forming a conically tapered root canal, the torque requirements of the file are reduced since the active file surfaces in contact with the wall of the root canal are interrupted by the zones of reduced file external diameter. By reducing the length of contact of the file active surfaces with the wall surfaces of root canal the possibility of the creation of a stall or lock-up in root canal is reduced. Thus, the chances that a file will develop sufficient resistance to torque to cause the file to be twisted off is substantially reduced.

The claims and the specification describe the invention presented and the terms that are employed in the claims draw their meaning from the use of such terms in the specification. The same terms employed in the prior art may be broader in meaning than specifically employed herein. Whenever there is a question between the broader definition of such terms used in the prior art and more specific use of the terms herein, the more specific meaning is meant.

While the invention has been described with a certain degree of particularly, it is manifest that many changes may be made in the details of construction and the arrangement of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

What is claimed is:

1. A reduced torque endodontic file for use in root canal therapy, comprising:
   an elongated metal shank having a proximate end for manipulating and rotating said file and a working portion terminating in a distal end, said working portion having a desired degree of taper toward said distal end, at least one flute extending helically about said working portion forming scraping edges thereupon, said working portion further including at least one reduced diameter zone, relative to adjacent working portions, having a desired axial length and extending about the circumference of said working portion.

2. The file of claim 1 further comprising a helical land axially adjacent said helical flute.

3. The file of claim 1 further comprising a plurality zones of reduced diameter, axially spaced along the working portion of said file.

4. The file of claim 3 wherein at least one of said zones of reduced diameter extends circumferentially around the full circumference of said file working portion.

5. The file of claim 3 wherein said axially spaced zones of reduced diameter are reduced in diameter by variable amounts.

6. The file of claim 5 wherein said reduced diameters decrease in amounts in proportion to the diameter of the said file in the direction toward said distal end.

7. The file of claim 3 wherein said axially spaced zones of reduced diameter are reduced in diameter by decreasing amounts in the axial direction toward said file distal end.

8. The file of claim 1 wherein said zone of reduced diameter is arcuate, V- or U-shaped in profile.

9. The file of claim 8 wherein said zone of reduced diameter is arcuate in profile.

10. The file of claim 1 wherein the zone of reduced diameter has a diameter that is reduced no more than the depth of said helical flute.

11. The file of claim 1 wherein said reduction in diameter is sufficient to at least substantially reduce frictional contact of said zones with root canal surfaces as said file is manipulated and rotated in said root canal.

12. A file for use in the endodontic preparation of a root canal, comprising:

an elongated metal shank having a handle end and a working portion tapering towards a distal end, the working portion having an external surface having at least one helical flute forming edges that, when in contact with the surfaces of a root canal wall, scrapes said canal wall surfaces to enlarge and shape the root canal, said working portion external surface including periodic reduced diameter zones where said helical scraping edges do not contact root canal wall surfaces, thereby reducing the fraction of working portion in contact with root canal wall surfaces.

13. The file of claim 12 wherein said working portion includes a land formed therein axially adjacent said helical edges.

14. The file of claim 12 wherein said periodic zones of reduced diameter are axially spaced and provide said working portion with an undulating outer profile.

15. A file of claim 12 wherein said axially spaced reduced diameter zones are each reduced in diameter at least sufficiently to substantially reduce frictional contact of said zone areas with root canal wall surfaces as said file is manipulated and rotated in said root canal.

16. A method of manufacturing a reduced torque input file for use in endodontic preparation of a root canal, comprising:

providing a metallic, elongated shank having a handle portion at one end and a working portion terminating in a distal end, said working portion having a desired rate of taper in millimeters per millimeter of working length;

forming on said working portion an undulating profile of reduced diameter zones, said profile generally decreasing in diameter towards said distal end; and forming on said undulating working surface at least one helical flute, providing at least one spiraled scraping edge, and an axially adjacent land.

17. A reduced torque endodontic file for use in root canal therapy, comprising:

an elongated metal shank having a proximate end for manipulating and rotating said file and a working portion terminating in a distal end, said working portion having a desired degree of taper toward said distal end, at least one flute extending helically about said working portion forming scraping edges thereupon, said working portion further including surface areas reduced relative to adjacent working portions such that frictional contact with canal walls during use is substantially reduced.

* * * * *